United States Patent [19]

Horwinski et al.

[11] 4,406,288
[45] Sep. 27, 1983

[54] BLADDER CONTROL DEVICE AND METHOD

[75] Inventors: Elwood R. Horwinski, Cheshire; Edward P. McGuire, Branford, both of Conn.

[73] Assignee: Hugh P. Cash, Cheshire, Conn. ; by said Elwood R. Horwinski

[21] Appl. No.: 251,324

[22] Filed: Apr. 6, 1981

[51] Int. Cl.³ .............................................. A61N 1/36
[52] U.S. Cl. .................................... 128/422; 128/788
[58] Field of Search ............... 128/419 E, 419 R, 420, 128/421, 422, 423, 788, 0.25

[56] References Cited

U.S. PATENT DOCUMENTS

| | | | |
|---|---|---|---|
| 2,771,554 | 11/1956 | Gratzl | 128/421 |
| 3,628,538 | 12/1971 | Vincent et al. | 128/419 E |
| 3,650,276 | 3/1972 | Burghele et al. | 128/419 E |
| 3,800,800 | 4/1974 | Garbe et al. | 128/421 |
| 3,933,147 | 1/1976 | DuVall et al. | 128/421 |

Primary Examiner—William E. Kamm
Attorney, Agent, or Firm—H. Gibner Lehmann; K. Gibner Lehmann

[57] ABSTRACT

An apparatus and method for conditioning the pelvic floor musculature of a living being to inhibit bladder contractility and relax the bladder so as to prevent involuntary urinary loss. The apparatus and method involve providing a pair of electrodes adapted for contact with tissue associated with the floor musculature. A steady, adjustable bias potential difference is applied to said electrodes, said potential difference having a value or amplitude which is less than a predetermined threshold value as the latter is established by a specific electrode orientation in or with relation to the tissue. Simultaneously with such application of bias voltage there is also applied to said electrodes a repeated adjustable intermittent potential, so as to cause resultant voltage values or peaks which are above the said threshold value. The sensory pathways to the spinal cord are thus uniquely stimulated, and also the motor pathways from the pelvic floor to the spinal cord, thereby to induce activity in another neutral pathway within the sacral spinal cord which is directly relaxing, or inhibitory to bladder contraction. Electronic means for carrying out the method comprises electrodes and solid state circuitry, the latter being adapted for battery energization. The apparatus is characterized by small size and light weight, and the adjustments allow for programming the applied energy to fit individual patient requirements.

20 Claims, 18 Drawing Figures

BLADDER CONTROL DEVICE AND METHOD

BACKGROUND

This invention relates to methods and devices for effecting a control of the bladder, for persons who are incontinent or otherwise in need of such assistance.

In the past, various devices have been proposed and produced for assisting a person who for one reason or another is no longer able to adequately control the bladder function. Some of these prior devices involved valving mechanisms intended to be implanted in or associated with the urethra. Other prior devices work differently, involving a conditioning of the responses of the individual patient in such a manner that muscle control is had, to accomplish the desired result.

Valves intended for implantation in the urethra in most cases cause considerable discomfort, and are not especially satisfactory even though the function that is desired, is attained. Also, valves and/or electrodes inserted in body cavities are uncomfortable, and in some cases can cause irritation and distress which detracts from the beneficial effect. The large size of many such prior devices has limited their usefulness due to the discomfort in addition to other drawbacks incidental to the external carrying of adjunct equipment. As a general rule, most prior devices did not represent a desirable solution to the problem, for the above reasons.

Moreover, these prior devices had limited capabilities since they could not provide electrical energy of different characteristics, to specifically suit the individual patient, and one or another particular kind of electrode disposition, arrangement or set of conditions.

SUMMARY

The drawbacks and disadvantages of prior methods and equipment for effecting urinary control are obviated by the present invention, which has for one object the provision of an improved method and apparatus for conditioning the pelvic floor musculature to control urinary loss, by which there is achieved a minimum amount of discomfort, while at the same time the functioning is especially effective for the desired purpose.

Another object of the invention is to provide an improved method and apparatus as above set forth, which has a beneficial and relaxing effect on related tissue and tends to promote recovery of voluntary bladder control.

A still further object of the invention is to provide an improved method, and an apparatus as characterized which is especially small and compact, and which can be selectively adjusted to provide different types of stimulation, so as to fit individual patient requirements and installations.

Yet another object of the invention is to provide an improved method and apparatus of the kind described, wherein the patient's threshold for excitation of the desired electrical response can be reduced, as by the utilization of a predetermined customized DC bias current.

In accomplishing the above objects the invention provides a pair of electrodes adapted for contact with tissue associated with the floor musculature. The electrodes may be part of an assemblage adapted for insertion in a body cavity, or the electrodes can be fine membrane-like members capable of insertion under the skin and retention thereunder with a minimum of discomfort, for transcutaneous stimulation. An adjustable means is provided for applying to said electrodes a bias potential difference having an amplitude below a predetermined threshold value, such as will result from a specific orientation of the electrodes in the tissue. Simultaneously with such application of a bias potential difference there is applied a repeated adjustable intermittent potential to said electrodes so as to cause resultant potential values or peaks which are above said threshold value. The electronic arrangement involves solid state devices and micro-circuitry arranged for excitation by a small battery. Adjustable means in the circuitry can change the amplitude and reverse the polarity of the DC bias, and can also alter the characteristics of the intermittent potential, thereby to achieve various different impulse effects on the tissue of the person, to achieve the desired response.

Other features and advantages will hereinafter appear.

In the accompanying drawings.

Figure 1:
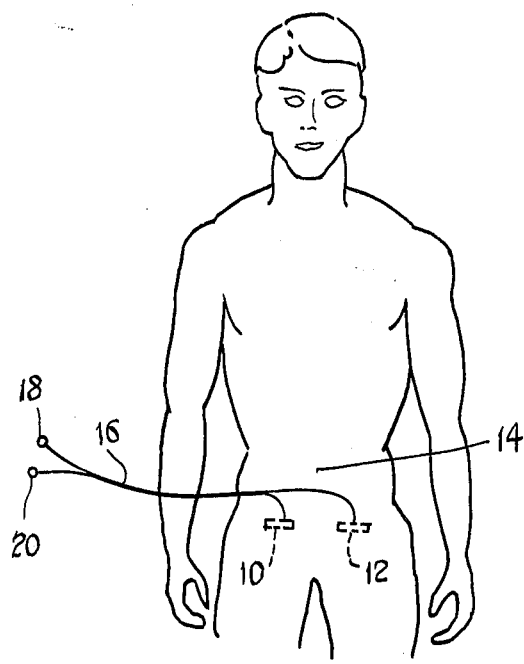
FIG. 1 is a diagrammatic representation of a person having a pair of fine membrane-like electrodes implanted in the abdominal wall and adapted to receive impulses for stimulation of the muscles of the pelvic floor musculature.

As shown in FIG. 1 a pair of fine, membrane-like electrodes 10, 12 making up an electrode pair is subcutaneously implanted in the abdominal wall 14, said electrodes being connected to a fine external lead cable 16 having terminals 18, 20 which latter can be joined to a miniature connector plug (not shown). The cable 16 is intended to receive energy from the circuitry shown in FIG. 5.

Figure 2:
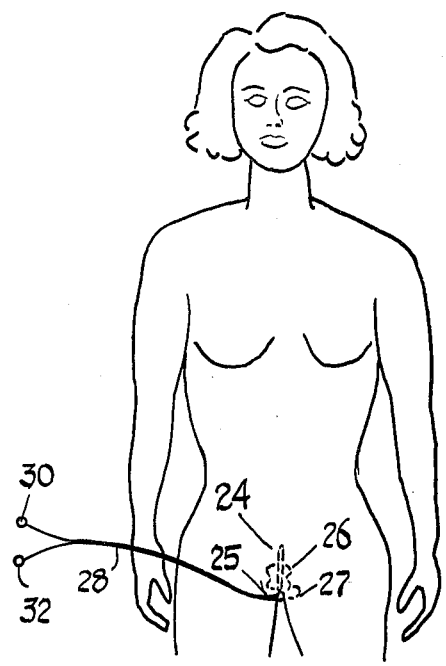
FIG. 2 is a view of a female person having vaginal and anal electrodes so located as to apply stimulation to adjoining body tissues, to effect bladder control.

In FIG. 2 a female person has electrodes 24, 26 arranged respectively in the vagina and anus, for contact with adjoining skin or tissue, and connected respectively by wires 25 and 27 to an external cable 28 having terminals 30, 32.

Figure 3:
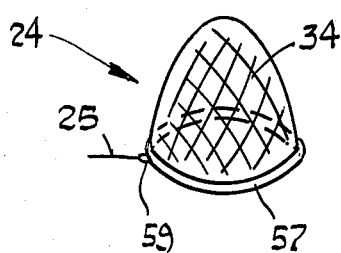
FIG. 3 is a perspective view of a wire-mesh type of vaginal electrode connected to a lead-wire.
Figure 4:
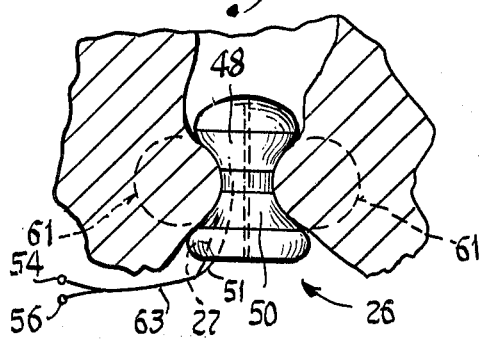
FIG. 4 is a side elevational view of an anal plug having electrodes connected with external leads.

FIG. 3 illustrates a wire mesh formation 34 of the electrode 24, connected by the wire 25 to the external cable 28. FIG. 4 shows the anal plug 26 having electrodes 48, 50 connected to wires 51 and 27, which can make up an external cable 63 provided with terminals 54, 56. Or, the wire 27 can be part of the cable 28 seen in FIG. 2.

The wire mesh formation 24 can comprise a generally conical or tubular construction of fine, conducting wires carrying a flexible circular base 57 preferably of resilient molded material provided with a terminal stub 59 from which the wire 25 emerges. The electrode 24 is so constructed as to be comfortably retainable in the vagina.

The anal plug 26 likewise has a resilient construction whereby it can be retained without discomfort in the anus, with the conducting surfaces 48, 50 of silver composition or other suitable material contacting spaced-apart areas of tissue at the sphincter muscle (designated by the broken outlines 61 in FIG. 4). The conducting surface 50 is normally connected to the inactive or grounding side of the excitation circuitry.

In accordance with the present invention a unique electronic excitation device is provided for connection with the cables 16, 28, 25, 27 or 63 to apply a composite, adjustable pulsed potential to the associated electrodes for the purpose of stimulating the sensory and motor pathways from the pelvic floor to the spinal cord, so as to induce inactivity in another neural pathway in the sacral cord which is directly relaxing, or inhibitory to bladder contraction. In consequence, a desired control of the bladder and urine is had. The excitation device, shown in FIG. 5, produces a DC bias voltage and current with adjustable polarity and amplitude, on which there is superposed a pulsed AC voltage and current that is also adjustable as to duration, frequency, time-interval and wave form. The total effect of the DC bias current is to reduce the threshold for excitation of the desired electrical response, and the adjustable character of both the DC bias supply and the pulsed AC supply allow for programming the device to suit individual patient requirements.

Figure 6:
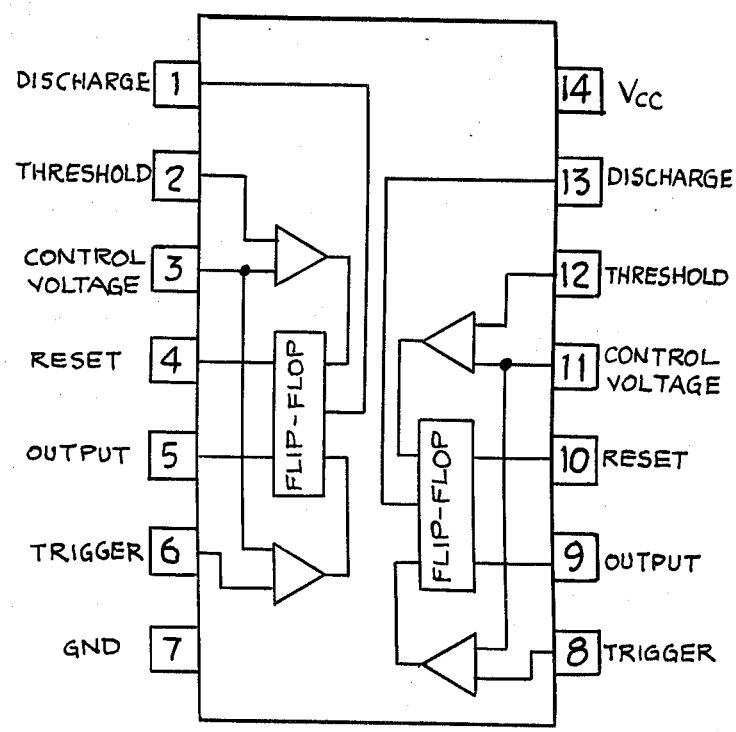
FIG. 6 is a wiring, block-type diagram of a duo-oscillator component of the device.
Figure 5:
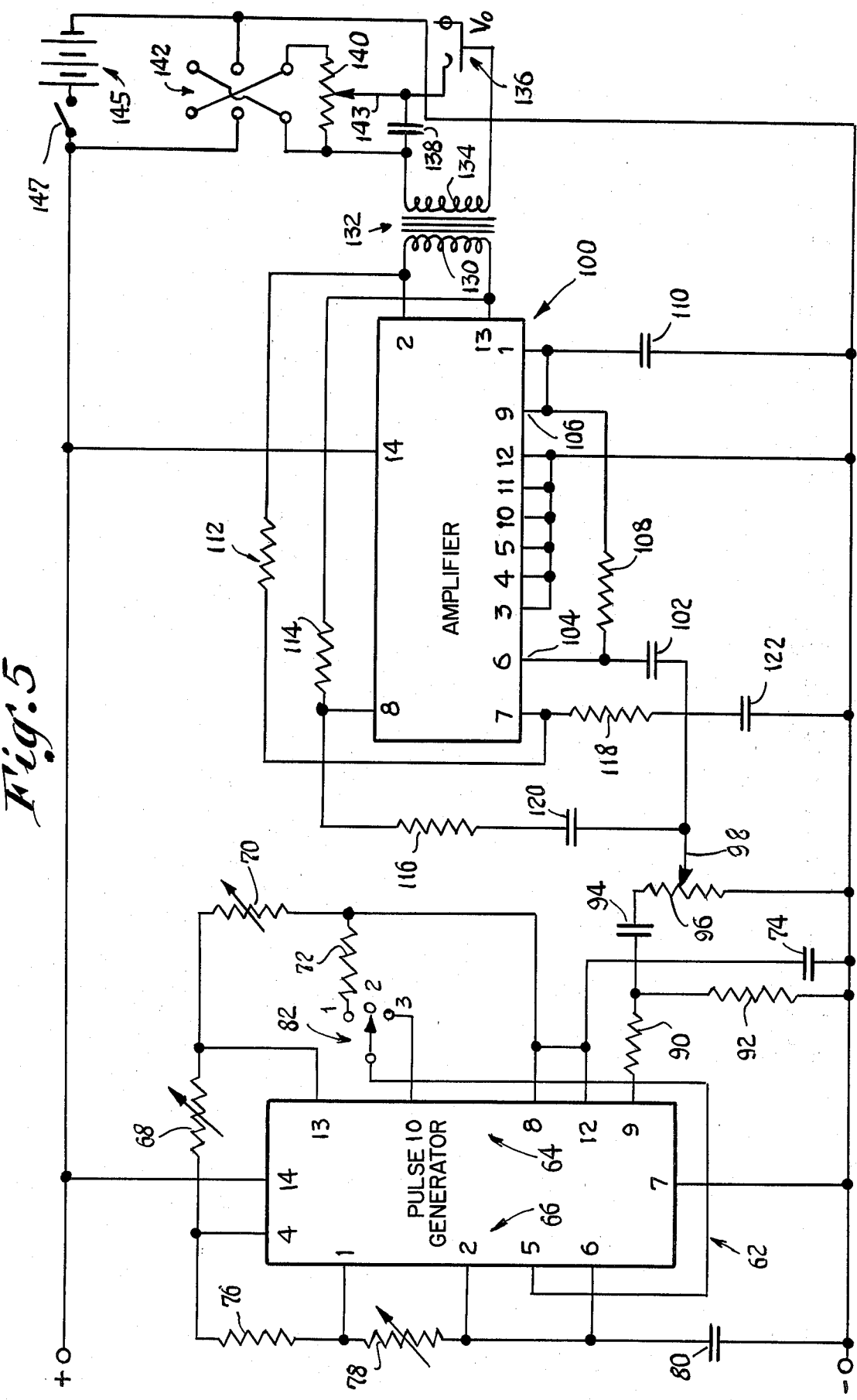
FIG. 5 is a schematic circuit diagram of a solid state apparatus by which both a steady bias potential is applied to the electrodes as well as an intermittent or pulsed potential, all for the purpose of stimulating and controlling the muscles and tissues to control the bladder.

Referring now specifically to FIG. 5 there is shown a DC and frequency generating apparatus which is especially suited for producing effective composite signals intended to be applied to the electrodes associated with the present apparatus. The device comprises an integrated circuit tone-burst generator 62, which can consist of two type 555 timers in a single package, known in the trade as a number 556. Such an item is currently available from Radio Shack Corporation, part No. 276-1728. A block-type wiring diagram of this component is illustrated in FIG. 6, showing the internal connections of each of the pins. The pin numbers in FIG. 5 refer to this particular unit.

Basically one of the timers 64 (namely that associated with pins 8–13 in FIG. 5) is connected as a free-running multivibrator intended to produce square wave signals in the range of from 65 to 1,000 cycles. The other timer 66 (represented by pins 1–6) is similary arranged to operate as a free-running multivibrator, with a substantially lower frequency, on the order of several cycles per second. Associated with the first multivibrator 64 are frequency-determining components including resistors 68, 70, 72, and a capacitor 74. Similarly, resistors 76, 78 and a capacitor 80 determine the frequency of oscillation of the second multivibrator 66.

Figure 15:
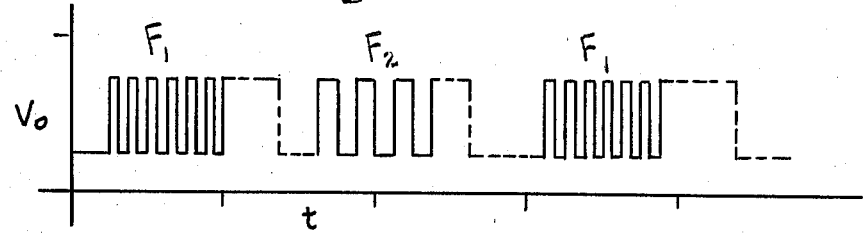
FIG. 15 is a graph showing the type of waveform that would be obtained from the circuit of FIG. 5, with the mode switch in the third of its three positions, wherein alternating bursts of different frequencies $F_1$ and $F_2$ are produced.

Also, associated with the multivibrators 64 and 66 is a three-position mode switch 82, connected so as to enable selective modulation of the multivibrator 64 by the multivibrator 66. The positions of the switch 82 are indicated by the numerals 1, 2 and 3. With the switch 82 in position No. 1, the timer 64 produces alternating bursts of square wave energy of two different frequencies. That is, a particular burst is generated having a frequency $F_1$, and a subsequent burst has a different, higher or lower frequency $F_2$. Such a condition is illustrated in FIG. 15 of the drawings, showing the wave forms associated with such operation.

With the switch in position No. 2, the output (pin 5) of multivibrator 66 is effectively disconnected from multivibrator 64, such that the latter can produce a continuous square wave frequency as determined by the resistors 70, 72, and capacitor 74.

With the mode switch 82 in position No. 3, the output of multivibrator 66 (pin 5) is merely used to gate the multivibrator 64 on and off. Accordingly there are produced periodic bursts of square wave signals of a single frequency, as determined by the value of the resistors 70, 72 and capacitor 74. The output of the multivibrator 64 is taken from pin 9, which has a load that includes resistors 90, 92, coupling capacitor 94, and potentiometer 96. The wiper 98 of the potentiometer carries an alternating signal received from pin 9 to a solid state, integrated-circuit type linear amplifier 100. This may be of the type known commercially as an LM 377 (Radio Shack Type LM 1877N-9, part No. 276-702). The pin numbers shown in FIG. 5 correspond to this unit.

The signal from the wiper 98 passes through a coupling capacitor 102 to the input 104 of the amplifier 100. A second input 106 is provided, and a biasing resistor 108 is connected between the two inputs. Also, a bypass capacitor 110 is connected from the input 106 to ground, as shown.

The amplifier 100 is arranged to have a differential output, pins 2 and 13. Feedback networks are provided, comprising resistors 112, 114, 116, 118, and capacitors 120, 122, which are involved with stabilizing the amplifier, and determining the shape of the frequency-gain characteristics.

The output from pins 2 and 13 is applied to the low-impedance winding 130 of an output transformer 132, which has a secondary winding 134. The nature of the signal being carried by the transformer 132 is bursts of square wave energy, or alternately, a continuous square wave signal, depending on the position of the mode switch 82. By the present invention, a DC voltage or bias can be imparted to the signal from the transformer 132, so as to sum with the AC component, and in effect shift the average value of the resultant output signal that will appear ultimately on output jack 136, to different desired levels.

In accomplishing the summing operation wherein the square wave signal is added to or subtracted from a DC level, there is provided in the output winding 134 a blocking capacitor 138 which functions to couple only the AC component from the winding 134, (and not the DC component, which of course would be zero). A potentiometer 140 is provided, and a polarity reversing switch 142 is connected as shown across the battery supply. It can be understood that with the switch 142 in the one position, the full battery supply voltage (typically 9 volts) will appear across the potentiometer 140, with a given polarity. Similarly, with the switch in the opposite position (not shown) the full battery voltage will appear across the potentiometer, but with the opposite polarity. Accordingly, on the wiper 143, it will be possible to algebraically sum a fraction of the 9 volt supply voltage as determined by the position of the wiper 143, with the square wave signal coming through the blocking capacitor 138, such that there will appear on the output jack 136 a composite signal similar to that shown in one fo the FIGS. 7–15.

As presently understood, it is important to be able to set a particular DC level to the signal that is applied to the electrodes, which level will be slightly below a threshold value that will depend upon the sensitivity of the particular patient, the patient's condition, and the exact location of the electrodes. This threshold value will in all likelihood, be determined experimentally. In addition, the capability for adjusting the nature of the square wave signals is important from the standpoint of providing the proper, desired stimulation to the muscles. Also, it is assumed that the present apparatus may be employed with electrodes having different relative spacing, and at different locations on the body of the patient. Accordingly the ability to adjust the nature of the signals that are applied to these electrodes is an important feature of the present invention.

FIGS. 7–15 show some of the waveforms that can be generated by the circuit of FIG. 5. These forms are given as examples only and should not be considered limiting, as other waveshapes such as sine waves and triangular waves could also be employed in the practice of the present invention, as can be readily understood.

Figure 7:
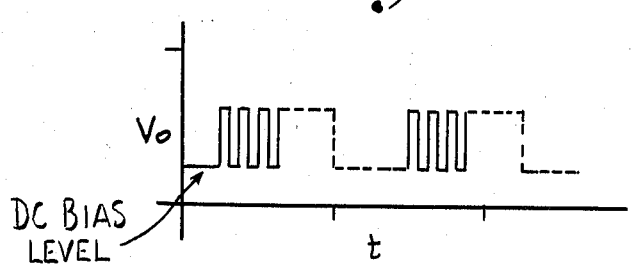
FIGS. 7–9 are graphs of waveforms of the type which would be obtained from the circuit in FIG. 5, with the mode switch thereof in one of its three positions.

FIG. 7 illustrates a burst of square wave energy similar to that which would be obtained were the mode switch 82 placed in the No. 3 position. The waveform is a modulated square wave, the square wave having a frequency typically in the neighborhood of from 65 to 1000 cycles, and the modulating frequency being one or several cycles. There is a DC component to the wave, the polarity of which is set by the switch 142, and the magnitude of which is determined by the potentiometer 140. The amplitude of the square wave is set by means of the potentiometer 96.

Figure 8:
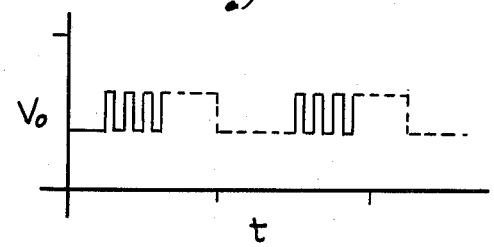

FIG. 8 shows a similar wave shape, except that the amplitude of the square wave is less, as determined by the setting of the potentiometer 96, and the DC component is higher, as set by the potentiometer 140.

Figure 9:
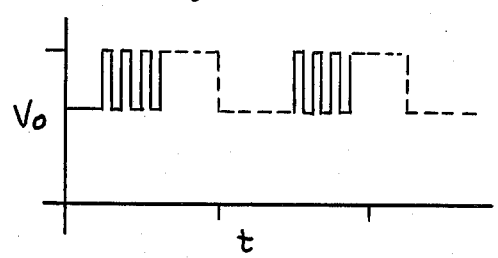

FIG. 9 illustrates a still higher DC component of the composite wave, with the amplitude (peak-to-peak) of the square wave being substantially the same as that in FIG. 7.

Figure 10:
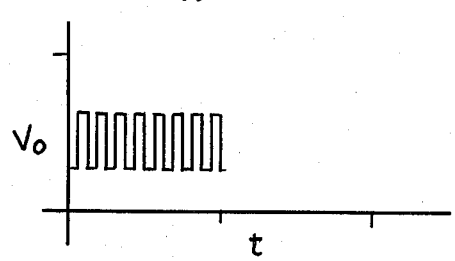

FIG. 10 indicates the nature of the signal that would be produced if the mode switch 82 were shifted to the No. 2 position. The circuit then produces a continuous square wave, no modulation, having a DC component determined by the setting of the potentiometer 140.

Figure 11:
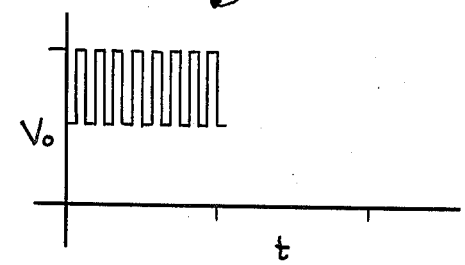
FIGS. 10 and 11 are graphs similar to those of FIGS. 7–9, except with the mode switch in another of its three positions.

FIG. 11 is similar to FIG. 10, but with an increased amplitude (peak-to-peak) of square wave, as obtained by adjusting the potentiometer 96.

Figure 12:
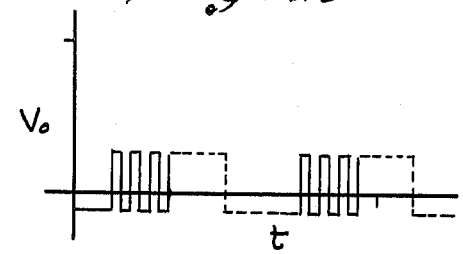
FIGS. 12–14 are graphs similar to those of FIGS. 7–9, and illustrating waveforms of different peak-to peak amplitude, and having distinct DC components associated therewith. These waveforms would be obtained with the mode switch of the circuit of FIG. 5 in the same position as that for which the waveforms of FIGS. 7–9 were obtained.

FIG. 12 shows a signal similar to FIG. 7, except that the DC component of the wave has been shifted to a small negative value such that the bottom half of the square wave extends below the baseline representing zero volts, and reaches a slightly negative instantaneous voltage, with respect to ground.

Figure 13:
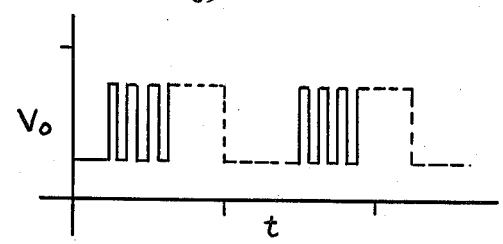

FIG. 13 is similar to FIG. 7, except that the amplitude of the square wave has been increased, by adjustment of the potentiometer 96.

Figure 14:
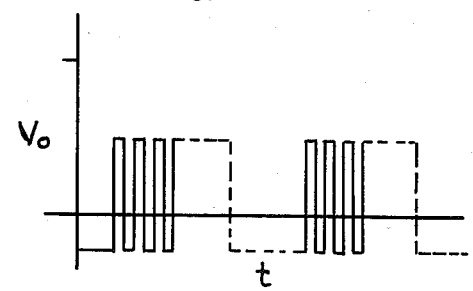

FIG. 14 shows a still larger-amplitude square wave, except with the DC component of the square wave having been lowered, such that negative portions of the wave extend below the baseline, as shown.

FIG. 15 is a plot of a waveform similar to that which would be obtained were the mode switch 82 set to the No. 1 position. The wave is characterized by alternating bursts of square wave energy of different frequencies, the first being a frequency $F_1$, and the second being a frequency $F_2$, where $F_1 \neq F_2$. The burst rate is determined by the setting of the potentiometer 78.

While all of the illustrated waveforms involve square waves, it can be readily understood that other types of forms can be employed, such as sine waves, triangular waves, unsymmetrical square waves, etc., and having DC components either above or below the baseline that represents ground potential.

In practicing the present invention, the nature of the particular signal to be used can be determined by experiment, and under conditions of actual use with the patient. The nature of the signal that is chosen will be tailored to provide the desired characteristics, and will depend upon the spacing of the electrodes, the location of the electrodes, and the nature of the condition which is being controlled or treated. In addition, the sensitivity of the patient to electrical stimulus will also be a determining factor of the optimum levels of the signals to be employed.

When the signals are being applied to the electrodes, the contraction of the bladder is inhibited, and accordingly retention of urine therein can occur. Upon the signals being discontinued, the voiding can take place.

Figure 17:
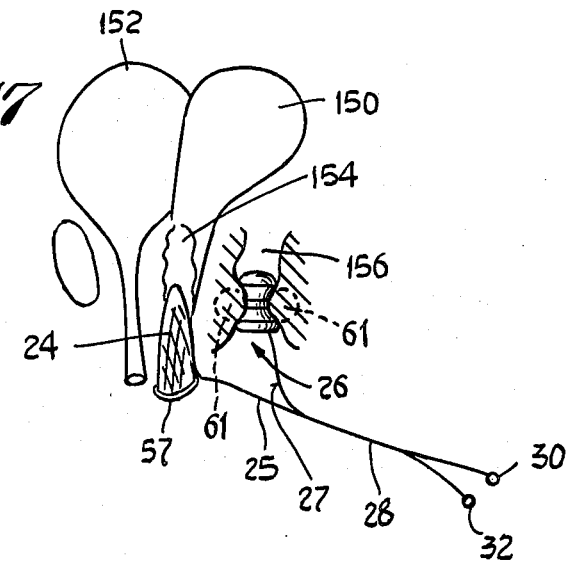
FIG. 17 is a diagrammatic representation of the bladder, uterus, vagina and rectum of a female person, with related electrode devices.

Referring particularly to FIG. 1, the excitation apparatus of FIG. 5 can be connected with the cable 16 so as to apply pulses to the subcutaneous electrodes 10, 12 located in the abdominal region. With regard to FIG. 2, the cable 28 can be connected with the excitation apparatus whereby the active lead 25 that is joined to the wire mesh cone 24 applies active pulses in the vaginal region, whereas the lead 27 connected with the conducting surface 50 of the anal plug 26 (see also FIG. 4) is the passive portion of the circuit that contacts the exterior region of the sphincter muscle 61. These connections are also illustrated in FIG. 17, which diagramatically depicts the locations of the uterus 150, the bladder 152, the vagina 154, and the rectal region 156.

Figure 16:
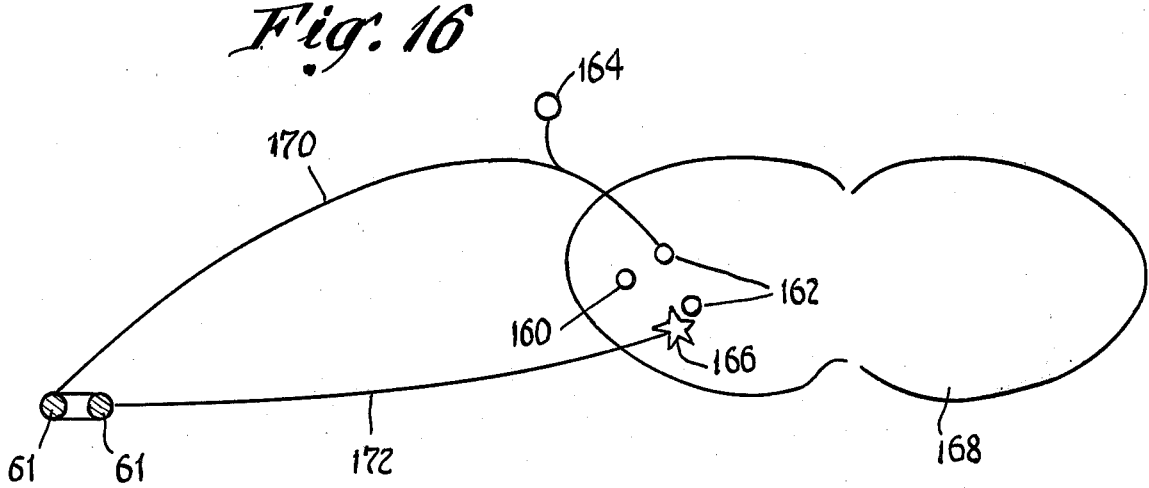
FIG. 16 is a diagrammatic representation of a spinal column in cross section, and associated motor and sensory nerves.

FIG. 16 illustrates diagramatically the location of the bladder motor nerve 160, the inhibitory nerves 162 and the pudendal sensory nerve 164, as well as the pudendal motor nerve 166 at or in the spinal column 168. The lines 170 and 172 are intended to indicate the pulse paths from the sphincter muscle 61 where the anal plug 26 is utilized, this being for example in connection with a male patient where the wire mesh 24 is not present. In such case, the two conducting surfaces 48, 50 of the plug 26 are connected respectively to the active and passive sides of the exciting circuitry, by means of the cable 63 (see FIG. 4).

Figure 18:
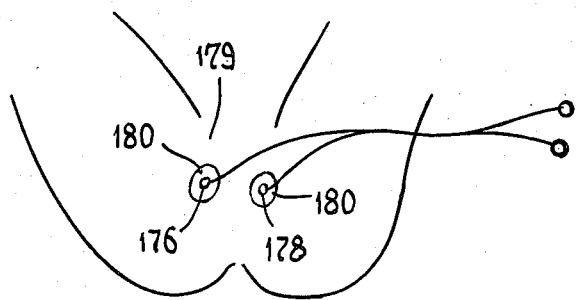
FIG. 18 is a diagrammatic representation showing pasted-on pirineal electrodes in the crotch region.

In FIG. 18, foam-backed paste-on electrodes 176 and 178 are seen as applied to the crotch region 179 of the patient, to deliver current to the pelvic floor musculature via the skin of the perineum. The electrodes 176 and 178 can consist of silver or silver chloride members which are carried by a foam backing 180 which is impregnated with adhesive material that allows for a topical direct application to the skin.

Relaxation of the bladder muscles can have a beneficial effect, especially in cases where stimuli occur too frequently and result in loss of tone of the musculature involved. By the use of the apparatus and method of the present invention it is possible to control bladder functioning in a manner which could improve the tone and help to regain normalcy.

From the above it can be seen that we have provided a novel apparatus and method for controlling muscle contractions in a desired, predetermined manner, the apparatus being physically small in size and of light weight construction. Such an arrangement lends itself to the capability of being easily carried by the patient, since the electronic unit is completely self-contained.

The present apparatus and method thus constitute a distinct advance and improvement in the technology of medical electronics.

Variations and modifications are possible without departing from the spirit of the invention.

We claim:

1. The method of conditioning the pelvic floor musculature of a living being, to inhibit bladder contractility so as to prevent involuntary urinary loss, comprising the steps of providing a pair of electrodes in contact with tissue associated with the floor musculature, applying a direct current bias potential difference to said electrodes, adjusting said direct current bias potential difference to a value below a predetermined threshold valuation as determined by the electrode orientation in the tissue, and simultaneously applying a repeated intermittent potential to said electrodes to cause resultant voltage values which are above said threshold valuation.

2. The method of claim 1, and including the further step of:
   (a) disposing the electrodes subcutaneously in the living being.

3. The method of claim 1, and including the further step of:
   (a) disposing the electrodes in at least one body cavity of the living being.

4. The method of claim 1, and including the further step of:
   (a) disposing the electrodes against the skin of the living being.

5. The method of claim 1, and including the further step of reversing the polarity of the energy applied to the electrodes.

6. The method of claim 1, and including the further step of altering the amplitude of the energy applied to the electrodes.

7. The method of claim 1, and including the further step of altering the wave form of the energy applied to the electrodes.

8. The method of claim 1, and including the further step of altering the frequency of the energy applied to the electrodes.

9. The method of claim 1, and including the step of applying the energy to the electrodes in the form of bursts of pulses.

10. The method of claim 9, and including the step of altering the time between the said bursts of pulses.

11. An apparatus for conditioning the pelvic floor musculature of a living being to inhibit bladder contractility so as to prevent involuntary urinary loss, comprising in combination:
    (a) a pair of electrodes adapted for contact with tissue associated with the floor musculature,
    (b) means for applying to said electrodes a direct current bias potential difference,
    (c) means for adjusting said direct current bias potential difference to a value below a predetermined threshold valuation as determined by the electrode orientation in the tissue, and
    (d) means for simultaneously applying repeated intermittent potential bursts of predetermined pulse width to said electrodes to cause resultant values thereon which are above said threshold valuation.

12. The invention as defined in claim 11, and further including:
    (a) means for reversing the polarity of the direct current bias potential on said electrodes.

13. The invention as defined in claim 11, and further including:
    (a) means for varying the amplitude of said direct current bias potential on said electrodes.

14. The invention as defined in claim 11, and further including:
    (a) means for adjusting the electrical frequency of the intermittent potential.

15. The invention as defined in claim 11, and further including:
    (a) means for adjusting the duration of the bursts.

16. The invention as defined in claim 11, and further including:
    (a) means for altering the wave form of said intermittent potential bursts.

17. The invention as defined in claim 11, and further including:
    (a) means for altering the width of the pulse.

18. The invention as defined in claim 11, and further including:
    (a) means for altering the amplitude and wave form of the voltage applied to said electrodes.

19. The invention as defined in claim 18, and further including:
    (a) means for reversing the polarity of the voltage applied to said electrodes.

20. The invention as defined in claim 11, wherein:
    (a) said means for applying the bias potential difference comprises a battery and a potentiometer energized from the battery.

* * * * *